| United States Patent [19] | [11] Patent Number: 4,576,914 |
| Yoshida et al. | [45] Date of Patent: Mar. 18, 1986 |

[54] METHOD FOR ENHANCING A FUNGUS-LYTIC ACTIVITY OF β-1,3-D-GLUCANASE

[75] Inventors: Akiyoshi Yoshida, Nara; Shigeru Kametaka; Shin'ichi Hayashi, both of Osaka, all of Japan

[73] Assignee: Rohto Pharmaceutical Co., Ltd., Japan

[21] Appl. No.: 542,861

[22] Filed: Oct. 17, 1983

[30] Foreign Application Priority Data

Oct. 18, 1982 [JP] Japan ................ 57-183421

[51] Int. Cl.[4] ............... C12P 39/00; C12N 9/24; C12N 1/06; C12R 1/06; C12R 1/125; C12R 1/645; C12R 1/685; C12R 1/885
[52] U.S. Cl. .................... 435/42; 435/200; 435/259; 435/824; 435/830; 435/839; 435/911; 435/917; 435/945
[58] Field of Search .............. 435/200, 42, 259

[56] References Cited

U.S. PATENT DOCUMENTS

| 3,761,353 | 9/1973 | Noe et al. ................... 435/42 |
| 3,969,189 | 7/1976 | Kobayashi et al. ............ 435/200 X |
| 4,067,773 | 1/1978 | Martin ...................... 435/200 X |
| 4,110,163 | 8/1978 | Hjortshoj et al. ............ 435/200 |
| 4,335,101 | 6/1982 | Stoudt et al. ............... 435/200 X |
| 4,486,330 | 12/1984 | Yoshida et al. ............. 435/200 |

*Primary Examiner*—Lionel M. Shapiro
*Attorney, Agent, or Firm*—Lawrence Rosen

[57] ABSTRACT

A method of enhancing a fungus-lytic activity of β-1,3-D-glucanase which comprises using said glucanase in the presence of one or more of the activators selected from the group consisting of sodium lauroylsarcosinate, polyoxyethylene alkylphenyl ether, polyoxyethylene alkyl ether, polyoxyethylene polyoxypropylenealkyl ether, benzalkonium chloride, ammonium chloride, chlorhexidine glucuronate, methylparaben, propylparaben, trypsin, Pronase ® and Alcalase ®.

A method of enhancing a fungus-lytic activity of β-1,3-D-glucanase which comprises using two β-1,3-D-glucanases of different origins is also provided.

8 Claims, 1 Drawing Figure

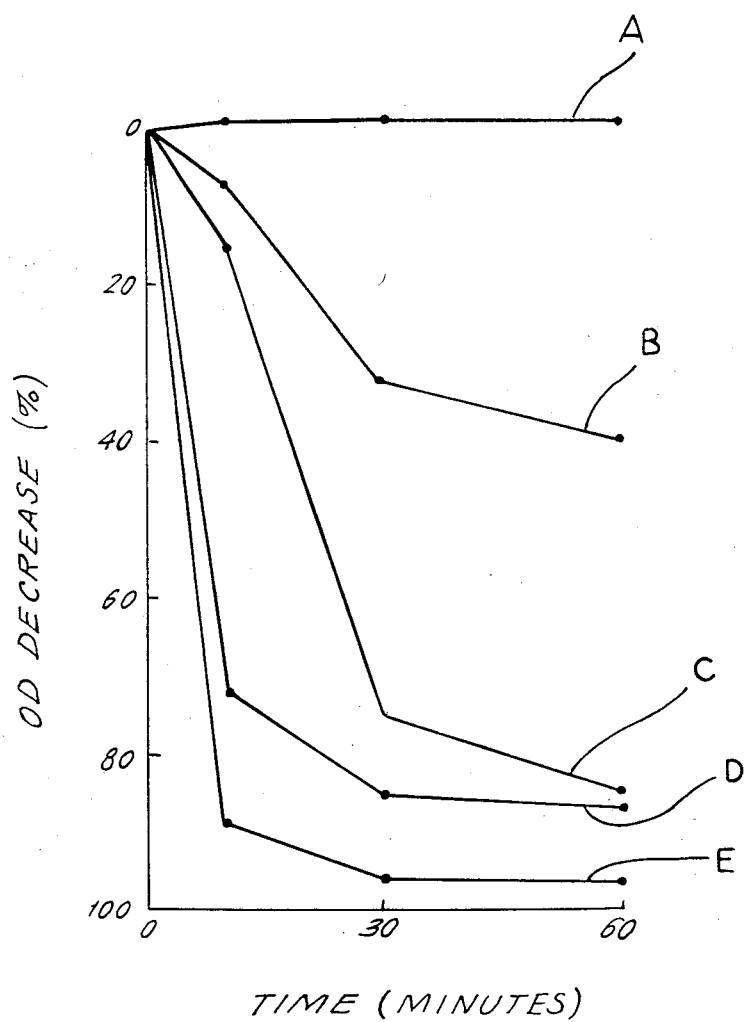

METHOD FOR ENHANCING A FUNGUS-LYTIC ACTIVITY OF B 1,3-D-GLUCANASE

The present invention relates to a method for enhancing a fungus-lytic activity of β-1,3-D-glucanase known as a hydrolase.

β-1,3-D-Glucanase, which is also referred to as β-1,3-glucan hydrolase, β-1,3(4)-glucan glucanohydrolase, or laminaranase, is an enzyme derived from various microorganisms. The enzyme has a capability of dissolving or destroying the cell wall of fungi(i.e., Eumycetes), especially in yeast form, and even fungi themselves under a lower osmotic pressure. This action of the enzyme to destroy fungi is hereinafter referred to as "fungus-lytic activity" in contrast to the existing term "bacteriolytic activity" associated with the destruction of bacteria.

The enzyme, β-1,3-D-glucanase, has been extensively employed in various fields for different purposes. For example, in a brewing industry, the enzyme has been employed for rinsing a fermentation tank or a filter medium; in a food or medicinal industry, it has been employed for removing the cell wall of fungi such as yeast under mild conditions because the cell wall makes it difficult to extract various physico-chemically instable nutrients, vitamines and enzymes from the cell; and in a microbiological industry, it has been employed for preparing protoplasts required for cell fusion(i.e., cytogamy) or introduction of an extranuclear gene. In addition, the enzyme has recently been employed as a cleaning agent for an artificial denture(see Japanese Patent Publication(Kokai) No. 134014/1983).

The enzyme, β-1,3-D-glucanase, can be obtained from various microorganisms(See, for instance, A. E. Moore and B. A. Stone, Biochem. Biophys. Acta, 258:238–247, 1972; J. P. G. Ballesta and M. Alexander, Trans. Br. Mycol. Soc., 58:481–487, 1972; K. Horikoshi and Y. Atsukawa, Agr. Biol. Chem., 37:1449–1456, 1973; G. H. Fleet and H. J. Phaff, J. Bacteriol., 119:207–219, 1974; T. Obata, K. Fujioka, S. Hara and Y. Namba, Agr. Biol. Chem., 41:671–677, 1977; and Japanese Patent Publication(Kokai) No. 2310/1979), and is commercially available, for instance, under the following trade names: Zymolyase ® 5000 and Zymolyase ® 60000, both derived from *Arthrobacter luteus*(Kirin Brewery Co., Ltd., Japan); YL-5 ® derived from *Achromobacter iunatus*(Amano Seiyaku Co., Ltd., Japan); Celefro ® derived from *Bacillus subtilis*(Novo Industri A/S, Denmark); Finizym ® derived from *Aspergillus nigar*(Novo Industri A/S, Denmark); Novozym ® 234 derived from *Trichoderma harzianum*(Novo Industri A/S, Denmark); and Kitalase ® derived from *Rhizoctonia solani* (Kumiai Chemical Industry Co., Ltd., Japan).

The commercially available enzymes listed above are all employable in the aforementioned applications. However, those having a quality of industrial grade exhibit a low potency and those of reagent grade are very expensive although they exhibit a high potency. Therefore, various methods for enhancing the fungus-lytic activity possessed by the enzyme have hitherto been proposed. For example, T. Kaneko, K. Kitamura and Y. Yamamoto, Agr. Biol. Chem., 37:2295–2302, 1973, disclosed that the fungus-lytic activity of the enzyme on living *Candida lipolytica* increased more than 10 to 20% by the addition of a reducing agent such as 2-mercaptoethanol, sodium thioglycolate or cysteine and that the susceptity of yeasts to the enzyme increased by the pre-treatment of the yeasts with a certain surface-active agent. Further, K. Kitamura and Y. Yamamoto, Agr. Biol. Chem., 45:1761–1766, 1981, disclosed that the fungus-lytic activity of the enzyme on a baker's yeast increased about 50% by the combined use of sodium sulfite and potassium chloride.

Although the prior art methods mentioned above are all useful for enhancing the fungus-lytic activity of β-1,3-D-glucanase, they have the following unnegligible drawbacks. The reducing agents are generally expensive and have a limited application. The surface active agents listed by T. Kaneko et al., in the aforementioned literature, as being a useful enhancing agent for β-1,3-D-glucanase activity, such as sodium dodecylsulfate, sodium dodecylbenzenesulfonate, cetyltrimethylammonium chloride, cetylpyridinium bromide, Tween 20 and Tween 80, have only a weak enhancing activity.

Therefore, additional enhancing agents for β-1,3-D-glucanase having a higher potency have long been desired.

The inventors have investigated a variety of chemical substances and found that the following substances are useful as an enhancing agent on the fungus-lytic activity of β-1,3-D-glucanase:

1. Anionic surfactants of N-acylsarcosine series, such as sodium lauroylsarcosinate;
2. A nonionic surfactant selected from the group consisting of polyoxyethylene alkylphenyl ether(PAPE), polyoxyethylene alkyl ether(PAE) and polyoxyethylene polyoxypropylenealkyl ether;
3. A cationic germicide selected from the group consisting of benzalkonium chloride, ammonium chloride and chlorhexidine glucuronate;
4. Antiseptics belonging to p-hydroxybenzoate series such as methylparaben and propylparaben;
5. Proteases of animal origin such as trypsin;
6. Proteases of microorganism origin such as Pronase ®(Kaken Seiyaku Co., Ltd., Japan) and Alcalase ®(Novo Industri A/S, Denmark).

Although each of the above compounds, which will be also referred to as "activator" hereinafter, can be effectively employed alone, the use of a mixture of two or more of these compounds is often more preferable. Preferred combinations are PAPE with chlorhexidine glucuronate, PAPE with benzalkonium chloride, PAE with chlorhexidine glucuronate, and PAE with benzalkonium chloride. Most preferred combinations are PAPE with chlorhexidine glucuronate and PAPE with benzalkonium chloride.

In addition, the inventors have also found that a combined use of two β-1,3-D-glucanases of different origins, for example, Zymolyase ® 5000 and Kitalase ®, shows synergism, namely, remarkably increased fungus-lytic activity than expected from each activity.

Thus, one of the objects of the present invention is to provide a method of enhancing a fungus-lytic activity of β-1,3-D-glucanase which comprises using said glucanase in the presence of one or more of the activators listed above.

Another object of the invention is to provide a method of enhancing a fungus-lytic activity of β-1,3-D-glucanase which comprises using two β-1,3-D-glucanases of different origins.

BRIEF DESCRIPTION OF THE DRAWING

FIG. 1 is a graph showing a synergistic effect of the combined use of PAPE and chlorhexidine glucuronate on the fungus-lytic activity of β-1,3-D-glucanase.

The following detailed examples are presented by way of illustration of certain specific embodiments of the invention.

In the following examples, Candida albicans IFO 1385, Candida tropicalis IFO 1400, Candida guilliermondii IFO 0566, Torulopsis inconspicua IFO 0621, Torulopsis glabrata IFO 0622 and Saccharomyces cerevisiae A224A, all in logarithmic growth phase, were employed as a substrate in testing fungus-lytic activity of β-1,3-D-glucanase. These microorganisms were obtained from the Department of Oral Bacteriology, Dental School, Hiroshima University, Japan.

EXAMPLE 1

ENHANCING ACTION OF VARIOUS COMPOUNDS ON THE FUNGUS-LYTIC ACTIVITY OF β-1,3-D-GLUCANASE

Candida albicans IFO 1385 strain was pre-incubated on Sabouraud's glucose medium(Difco), and the resultant cells in logarithmic growth phase were centrifuged, washed with distilled water, and suspended in distilled water so as to render the turbidity of the suspension to read 1.0 at 660 nm.

To 3 ml of the suspension were added 1 ml of a β-1,3-D-glucanase(Zymolyase ® 5000) solution in 50 mM phosphate buffer and 1 ml of the same buffer solution containing an activator listed in Table I. The mixture was incubated at 37° C. and turbidity of the suspension at 660 nm was measured 10 and 30 minutes after the initiation of the incubation. The fungus-lytic activity of β-1,3-D-glucanase was calculated according to the following equation in terms of the turbidities as measured, and the results were summarized in Table I.

Fungus-Lytic Activity = Decrease of $OD(\%)$ =

$$\frac{OD_i - OD_t}{OD_i} \times 100$$

$OD_i$: Optical Density(Turbidity) at 660 nm at an initiation time of the incubation
$OD_t$: Optical Density at 660 nm t minutes after initiation of the incubation.

TABLE I

Enhancing effect of various activators on fungus-lytic activity of β-1,3-D-glucanase

| Activators | Concentration (%) | Decrease of OD (%) after 10 minutes | Decrease of OD (%) after 30 minutes |
| --- | --- | --- | --- |
| Anion Surfactant: | | | |
| Sodium lauroyl- | 0.025 | 14.5 | 44.2 |
| sarcosinate | 0.05 | 29.0 | 61.3 |
| | 0.1 | 45.0 | 72.7 |
| Nonionic Surfactant: | | | |
| PAE*[1] | 0.05 | 35.0 | 83.0 |
| | 0.1 | 44.4 | 88.0 |
| | 0.5 | 50.6 | 90.0 |
| PAPE*[2] | 0.05 | 15.6 | 75.0 |
| | 0.1 | 16.3 | 76.5 |
| | 0.5 | 10.9 | 71.7 |
| Cationic Germicide: | | | |
| Benzalkonium | 0.001 | 67.7 | 82.3 |
| chloride | 0.005 | 25.3 | 34.9 |
| | 0.01 | 17.3 | 26.3 |
| | 0.05 | 17.0 | 26.0 |
| | 0.1 | 13.2 | 23.4 |
| | 0.5 | 12.0 | 23.0 |
| Chlorhexidine | 0.001 | 72.3 | 85.2 |
| glucuronate | 0.005 | 29.1 | 36.4 |
| | 0.01 | 17.7 | 24.4 |
| | 0.05 | 15.5 | 21.3 |
| | 0.1 | 9.3 | 12.6 |
| | 0.5 | 5.0 | 12.3 |
| p-Hydroxybenzoate: | | | |
| Methylparaben | 0.01 | 9.0 | 28.5 |
| | 0.02 | 9.4 | 45.3 |
| | 0.03 | 10.7 | 48.9 |
| | 0.04 | 9.9 | 49.3 |
| Propylparaben | 0.01 | 9.1 | 47.3 |
| Protease: | | | |
| Trypsin | 10 μ/ml | 23.0 | 51.0 |
| | 50 μ/ml | 28.3 | 68.6 |
| Pronase[R] | 10 μ/ml | 25.0 | 60.2 |
| | 25 μ/ml | 27.2 | 65.3 |
| | 50 μ/ml | 31.2 | 71.8 |
| Alcalase[R] | 10 μ/ml | 24.6 | 57.2 |
| | 25 μ/ml | 29.3 | 68.3 |
| | 50 μ/ml | 33.5 | 75.0 |

*[1]BL-9EX[R] (Nikko Chemical Co., Ltd., Japan)
*[2]NP-10[R] (Nikko Chemical Co., Ltd., Japan)

All of the activators listed in Table I showed a remarkable enhancing activity upon the fungus-lytic activity of β-1,3-D-glucanase. It should be noted that both benzalkonium chloride and chlorhexidine glucuronate exhibited an enhancing action on the fungus-lytic activity of the enzymene at lower concentrations, whereas they lowered the activity of the enzyme at higher concentrations.

EXAMPLE 2

EFFECT OF A COMBINED USE OF TWO ACTIVATORS

The test results in Example 1 showed that both PAPE and chlorhexidine glucuronate exhibited a remarkable enhancing action on the fungus-lytic activity of β-1,3-D-glucanase. However, microscopic investigation of the suspension which was incubated for 30 minutes had been revealed that some yeast cells remained intact without receiving the fungus-lytic activity of the enzyme. Accordingly, it was tested according to the procedure disclosed in Example 1 as to whether or not a combined use of these two activators can result in a complete destruction of all of the yeast cells. The test results are shown in FIG. 1.

In FIG. 1, A, B, C, D and E represent the following meanings:

A ... PAPE(NP-10 ®) +Chlorhexidine glucuronate(-control)
B ... Zymolyase ® 5000(control)
C ... Zymolyase ® 5000 +PAPE
D ... Zymolyase ® 5000 +Chlorhexidine glucuronate
E ... Zymolyase ® 5000 +PAPE +Chlorhexidine glucuronate.

The final concentrations of Zymolyase ® 5000, PAPE and chlorhexidine glucuronate were 0.5 mg/ml, 0.05% and 0.001%, respectively.

FIG. 1 shows that a combined use of PAPE and chlorhexidine glucuronate exhibited extraordinarily strong enhancing activity on the fungus-lytic activity of the enzyme already in the early stage of incubation as compared with a single use of each of these activators and established an OD-decrease of more than 95% after 30 minutes incubation. Microscopic investigation revealed that almost all of the yeast cells were destroyed by the fungus-lytic activity of the enzyme.

A synergistic effect similar to that derived by the combined use of two activators as stated above was also given by the combination of chlorhexidine glucuronate with PAE, and of benzalkonium chloride with PAPE or PAE.

EXAMPLE 3

ENHANCING EFFECT OF VARIOUS ACTIVATORS ON THE FUNGUS-LYTIC ACTIVITY OF β-1,3-D-GLUCANASE OF VARIOUS ORIGINS.

The effect of the combined use of PAPE(NP-10 ®) and benzalkonium chloride on the fungus-lytic activity of β-1,3-D-glucanase of various origins was measured using six living microorganisms as a substrate. Table II below shows the test results.

TABLE II

Effect of the combined use of β-1,3-D-glucanase and activators on destuction of various organisms

| Microorganism | Zymolyase$^R$ 5000$^{(a)}$ − | Zymolyase$^R$ 5000$^{(a)}$ + PAPE$^{(d)}$ and Benzalkonium chloride$^{(e)}$ | Kitalase$^{R(b)}$ − | Kitalase$^{R(b)}$ + PAPE$^{(d)}$ and Benzalkonium chloride$^{(e)}$ | Novozym$^R$ 234$^{(c)}$ − | Novozym$^R$ 234$^{(c)}$ + PAPE$^{(d)}$ and Benzalkonium chloride$^{(e)}$ |
|---|---|---|---|---|---|---|
| Candida albicans IFO 1385 | 21.4$^{(f)}$ | 88.2 | 7.5 | 48.1 | 0 | 60.6 |
| C. tropicalis IFO 1400 | 1.4 | 79.6 | 0 | 13.8 | 0 | 31.9 |
| C. guilliermondii IFO 0566 | 66.2 | 98.9 | 13.5 | 71.2 | —$^{(g)}$ | — |
| Torulopsis glabrata IFO 0622 | 81.0 | 99.4 | 23.0 | 77.4 | — | — |
| T. inconspicua IFO 0621 | 4.7 | 99.0 | 22.6 | 83.8 | — | — |
| Saccharomyces cerevisiae A224A | 91.1 | 99.3 | 75.5 | 84.9 | — | — |

$^{(a)}$Zymolyase$^R$ 5000: 0.1 mg/ml
$^{(b)}$Kitalase$^R$ : 0.5 mg/ml
$^{(c)}$Novozym$^R$ 234: 0.5 mg/ml
$^{(d)}$PAPE: 0.5 mg/ml
$^{(e)}$Benzalkonium chloride: 10 μg/ml
$^{(f)}$OD decrease (%) after 30 minutes incubation
$^{(g)}$not tested Table II shows the following matters:

(a) The combined use of PAPE and benzalkonium chloride established the enhancement of the fungus-lytic activity of Zymolyase ® 5000 on all of the microorganisms listed in the table.

(b) The fungus-lytic activity of β-1,3-D-glucanase on Candida tropicalis IFO 1400 and Torulopsis inconspicua IFO 0621, which are generally less susceptible to the enzyme, increased 75% and 95%, respectively, when PAPE and benzalkonium chloride had been simultaneously employed.

(c) A similar enhancing effect as stated above was also observed in Kitalase ® and Novozym ® 234.

Thus, the activators of the invention are useful as an enhancing agent of the fungus-lytic activity of β-1,3-D-glucanase of various origins and applicable to all of the microorganisms listed in the table.

EXAMPLE 4

SYNERGISM OF THE COMBINED USE OF TWO β-1,3-D-GLUCANASE OF DIFFERENT ORIGINS

Zymolyase ® 5000 and Kitalase ® used in Example 3 are of different origins, and therefore, their fungus-lytic activity spectra are different from each other as shown in Table II. In addition, the optimum pH of the former(7.0) is different from that of the latter(6.0). Accordingly, the effect of the combined use of these two enzymes of different origins was investigated according to the procedure described in Example 1. Candida albicans IFO 1385 and Candida tropicalis IFO 1400 were employed as a substrate.

Table III below summarizes the results of the test. It will be apparent to those skilled in the art that the combined use of these two enzymes shows synergism, namely, remarkably intensified fungus-lytic activity over the sum of the activities possessed by the respective activators.

TABLE III

| | Synergism of two β-1,3-D-glucanases of different origins | |
|---|---|---|
| β-1,3-D-glucanase | Candida albicans IFO 1385 | Candida tropicalis IFO 1400 |
| (1) Zymolyase$^R$ 5000$^{(a)}$ | 21.4$^{(d)}$ | 1.4 |
| (2) Kitalase$^{R(b)}$ | 7.5 | 0 |
| (3) (1) + (2) (calculated) | 28.9 | 1.4 |
| (4) (1) + (2) (observed)$^{(c)}$ | 82.3 | 56.3 |

$^{(a)}$final concentration: 0.1 mg/ml
$^{(b)}$final concentration: 0.5 mg/ml
$^{(c)}$final concentration of (1): 0.1 mg/ml
final concentration of (2): 0.5 mg/ml
$^{(d)}$OD decrease (%) after incubated for 30 minutes at pH 6.5

What we claim is:

1. A method of enhancing a fungus-lytic activity of β-1,3-D-glucanase which comprises using two β-1,3-D-glucanases of different origins.

2. A method of enhancing a fungus-lytic activity of β-1,3-D-glucanase which comprises using said glucanase in the presence of one or more of the activators selected from the group consisting of sodium lauroylsarcosinate, polyoxyethylene alkylphenyl ether, polyoxyethylene alkyl ether, polyoxyethylene polyoxypropylenealkyl ether, benzalkonium chloride, ammonium chloride, chlorhexidine glucuronate, methylparaben and propylparaben.

3. A method according to claim 2 wherein said glucanase is derived from the group consisting of *Arthrobacter luteus, Achromobacter iunatus, Bacillus subtilis, Aspergillus nigar, Trichoderma harzianum* and *Rhizoctonia solani*.

4. A method according to claim 2 in which more than one activator is employed.

5. A method according to claim 4 in which one of said activators is polyoxyethylene alkylphenyl ether and the other of said activators is benzalkonium chloride or chlorhexidine glucuronate.

6. A method according to claim 4 in which one of said activators is polyoxyethylene alkyl ether and the other of said activators is benzalkonium chloride or chlorhexidine glucuronate.

7. A method of claim 1 wherein said glucanase is dervived from the group consisting of *Arthrobacter luteus, Achromobacter iunatus, Bacillus subtilis, Aspergillus nigar, Trichoderma harzianum* and *Rhizoctonia solani.*

8. A method according to claim 7 wherein one of said glucanases is derived from *Anthrobacter luteus* and the other glucanase is derived from *Rhizoctonia solani.*

* * * * *